US006068148A

United States Patent [19]

Weiler

[11] Patent Number: 6,068,148

[45] Date of Patent: May 30, 2000

[54] HERMETICALLY SEALED CONTAINER INCLUDING A NOZZLE WITH A SEALING BEAD

[75] Inventor: Gerhard H. Weiler, South Barrington, Ill.

[73] Assignee: Automatic Liquid Packaging, Inc., Woodstock, Ill.

[21] Appl. No.: 09/084,804

[22] Filed: May 26, 1998

[51] Int. Cl.[7] ................................ A61J 1/06; A61M 5/28

[52] U.S. Cl. ...................... 215/48; 215/DIG. 3; 141/346; 604/243; 604/905

[58] Field of Search ................................. 215/40–43, 45, 215/47–49, 317, 318, 321, DIG. 3; 206/528, 532; 222/386, 325, 567, 107; 604/240, 243, 212, 905; 141/346, 367, 370

[56] References Cited

U.S. PATENT DOCUMENTS

| | | | |
|---|---|---|---|
| 2,172,544 | 9/1939 | Panter | 215/317 |
| 3,083,858 | 4/1963 | Biedenstein | 215/48 X |
| 3,204,835 | 9/1965 | Michel | 215/48 X |
| 3,472,227 | 10/1969 | Burke | 604/243 |
| 3,524,445 | 8/1970 | Frieze | 604/212 |
| 3,756,235 | 9/1973 | Burke et al. | 604/240 |
| 3,905,370 | 9/1975 | Lazdowski | 604/212 |
| 3,987,930 | 10/1976 | Fuson . | |
| 4,335,824 | 6/1982 | Bush | 215/317 X |
| 4,643,309 | 2/1987 | Evers . | |
| 4,779,997 | 10/1988 | Schmidt | 215/317 X |
| 5,046,627 | 9/1991 | Hansen . | |
| 5,219,337 | 6/1993 | Takata et al. | 604/212 |
| 5,261,881 | 11/1993 | Riner | 604/212 X |
| 5,740,931 | 4/1998 | Weiler . | |
| 5,901,865 | 5/1999 | Weiler et al. | 215/48 |

FOREIGN PATENT DOCUMENTS

| | | | |
|---|---|---|---|
| 0 088 056 A1 | 9/1983 | European Pat. Off. . | |
| 0 591 156 B1 | 4/1994 | European Pat. Off. . | |
| 2533594 | 2/1976 | Germany | 604/243 |

*Primary Examiner*—Nathan J. Newhouse
*Attorney, Agent, or Firm*—Olson & Hierl, Ltd.

[57] ABSTRACT

A hermetically sealed, molded thermoplastic dispensing container is provided which includes a nozzle having a resilient and unitary annular bead about the periphery thereof. The nozzle is sized to receive the hub of a dispensing assembly in a mating relationship and the bead provides a secure friction fit and liquid seal between the hub and the nozzle. The method of forming a container with a nozzle having such a bead includes the use of seal molds having a groove conforming to the shape of the bead and a vacuum passage in communication with such groove and the step of creating a vacuum through the passage and the groove to pull a portion of a parison into the groove to form the bead.

9 Claims, 3 Drawing Sheets

HERMETICALLY SEALED CONTAINER INCLUDING A NOZZLE WITH A SEALING BEAD

FIELD OF THE INVENTION

This invention relates to hermetically sealed containers and, more particularly, to a dispensing container with a nozzle that includes a sealing bead.

BACKGROUND OF THE INVENTION

Hermetically sealed containers with luer tapered dispensing nozzles adapted to receive the hub of a hyperdermic needle assembly are known in the art. See, for example, FIG. 11 of U.S. Pat. No. 5,595,314 to Weiler which discloses a male luer connector adapted to receive the female hub of a hyperdermic needle. Internal threads in the connector engage lugs on the hub of the needle for securing the needle to the nozzle.

Although the connector shown in U.S. Pat. No. 5,595,314 has proven useful, a separate insert is required to provide the connector feature.

Hermetically sealed containers produced by the so-called blow/fill/seal techniques such as, for example, the blow/fill/seal techniques shown and disclosed in U.S. Pat. No. 4,671,763 to Weiler have gained widespread acceptance in the pharmaceutical field. Such containers are formed between cooperating molds that are closed around an extended length of a parison. This fabrication process, while efficient, necessarily results in a finished container with a mold seam or parting line.

The presence of such a seam on a dispensing nozzle is disadvantageous in applications where it is desired to mount a dispensing needle or spike on the nozzle because the seam may create a gap between mating surfaces through which liquid contents of the container can leak during the dispensing operation. It would thus also be desirable to provide a container with an improved nozzle that provides a liquid seal in the region of the mold seam. The present invention provides such an improved nozzle on a dispensing container.

SUMMARY OF THE INVENTION

A hermetically sealed, molded thermoplastic dispensing container embodying the present invention includes a nozzle unitary with the container, which nozzle defines a dispensing aperture. A removable closure unitary with the nozzle occludes the aperture, and a resilient annular bead about the periphery of the nozzle, unitary therewith and spaced from the aperture, provides a liquid seal for a dispensing needle or spike mounted thereto.

The nozzle is sized to receive a hub of a dispensing assembly such as, for example, a hypodermic needle assembly, in a mating relationship therewith. The annular bead provides a liquid seal between the hub and the nozzle.

In one embodiment of the present invention, the resilient bead has substantially a fin-like or triangular cross-section and includes spaced-apart upper and lower surfaces which extend radially outwardly from the outer surface of the nozzle at an obtuse angle and converge to an edge.

In one embodiment, the obtuse angle between the outer surface of the nozzle and the upper surface of the bead is approximately 120 degrees while the obtuse angle between the outer surface of the nozzle and the lower surface of the bead is approximately 135 degrees.

Other suitable bead embodiments are, for example, a bead where the lower surface of the bead extends radially outwardly from the outer surface of the nozzle substantially normal to the nozzle surface and the upper surface of the bead extends radially outwardly from the outer surface of the nozzle at an obtuse angle. The present invention also contemplates embodiments where the bead is syncline or rounded.

A container including the present features can be made by a method which includes the steps of extending a parison segment between main molds and seal molds, respectively, where the seal molds include a groove conforming to the shape of the bead and a vacuum passage which extends from the groove through the seal molds and closing the main molds to form a body portion of the container and then filling the body portion with a liquid. Next, the seal molds are closed to form the nozzle and seal the container. A vacuum is created through the passage and the groove in the seal molds to pull a portion of the parison into the groove and form the bead during the sealing operation.

Numerous other advantages and features of the present invention will become readily apparent from the following detailed description of the invention, from the claims, and from the accompanying drawings.

BRIEF DESCRIPTION OF THE DRAWINGS

In the accompanying drawings forming part of the specification, in which like numerals are employed to designate like parts throughout the same.

DETAILED DESCRIPTION OF THE PREFERRED EMBODIMENTS

Figure 1:
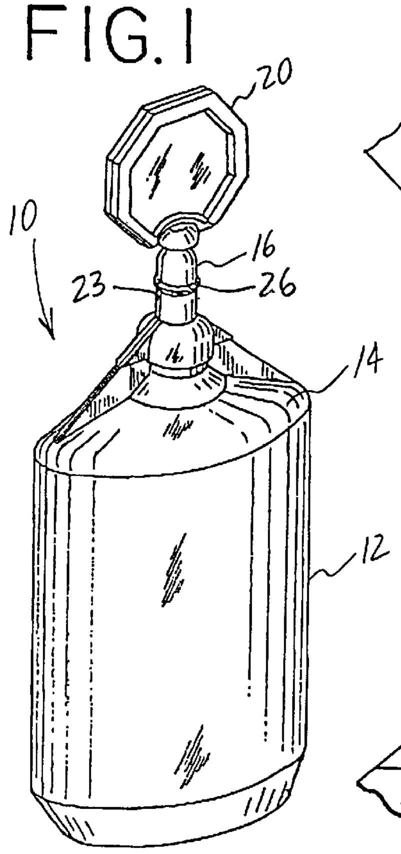
FIG. 1 is a perspective view of one embodiment of a container of the present invention in its blow molded, filled and sealed configuration.
Figure 2:
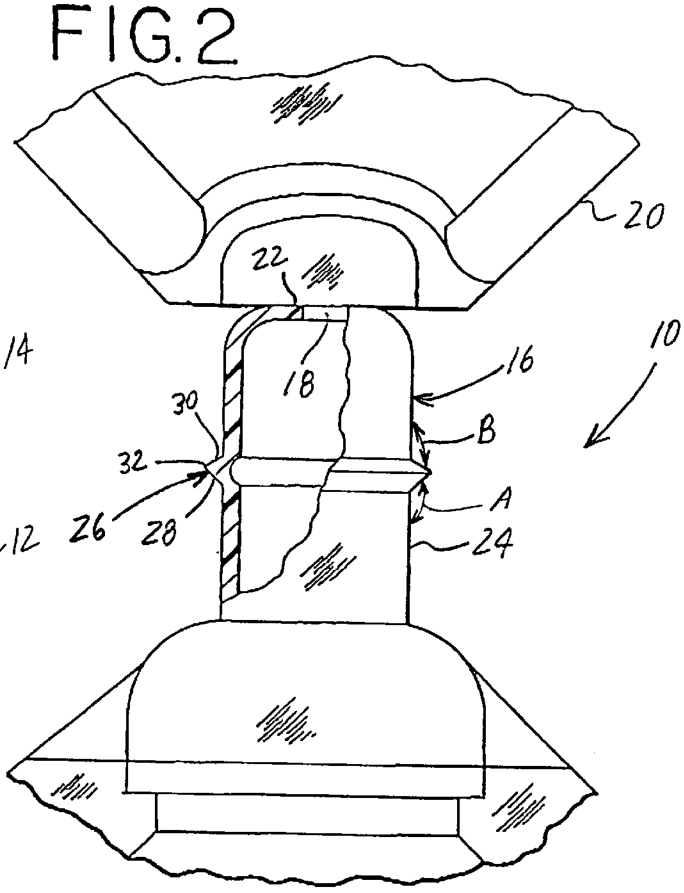
FIG. 2 is an enlarged fragmentary part sectional view of the nozzle and cap portion of the container of FIG. 1 in elevation.

Referring to FIGS. 1 and 2, a hermetically sealed, molded thermoplastic container 10 embodying the present invention includes a body portion 12, a neck portion 14 unitary with the body portion 12, a unitary stem or nozzle 16 extending in a direction away from the neck portion 14 and including an upper end defining a dispensing or draining aperture 18, and a removable twist-off overcap or closure 20 which occludes the aperture 18 and is unitary with the nozzle 16. The closure 20 is delineated by a frangible web 22.

Because the container 10 is fabricated by the so-called blow/fill/seal techniques such as, for example, the techniques shown and disclosed in U.S. Pat. No. 4,671,763 to Weiler which includes the use of cooperating molds, the container 10 includes a central peripheral mold seam or parting line 23.

The molded thermoplastic material can be a conventional molding material such as high density polyethylene, low density polyethylene, polypropylene, and the like, compatible with the contemplated container contents. Containers embodying the present invention can have a wide variety of shapes and capacities.

The invention disclosed herein is, of course, susceptible of embodiment in many different forms. Shown in the drawings and described hereinbelow in detail are preferred embodiments of the invention. It is to be understood, however, that the present disclosure is an exemplification of the principles of the invention and does not limit the invention to the illustrated embodiments.

For ease of description, the container 10 embodying the present invention is described hereinbelow in its usual assembled positions as shown in the accompanying drawings and terms such as upper, lower, horizontal, etc., will be used herein with reference to this usual position. However, the container may be manufactured, stored, transported, sold, or used in orientations other than those described and shown herein.

As shown in FIGS. 1 and 2, the nozzle 16 includes an outer peripheral surface 24 and a resilient, unitary annular bead 26 extending circumferentially and radially outwardly about the outer peripheral surface 24. The bead 26 is spaced from, and lies in a plane generally parallel to, the aperture 18 of the nozzle 16.

In the preferred embodiment of the present invention, the bead 26 has a substantially triangular or fin-shaped cross-section and includes spaced-apart lower and upper flat surfaces 28 and 30 respectively which converge radially outwardly at an obtuse angle from the nozzle outer surface 24 and include distal ends which terminate into an annular edge or tip 32. Particularly, the lower surface 28 extends unitarily outwardly from the outer nozzle surface 24 at an obtuse angle which is greater than the obtuse angle between the upper surface 30 and the outer nozzle surface 24. Preferably, the lower surface 28 extends away from the outer nozzle surface 24 at an angle A which is approximately 135 degrees while the upper surface 30 extends away from the outer nozzle surface 24 at an angle B which is approximately 120 degrees.

Figure 3:
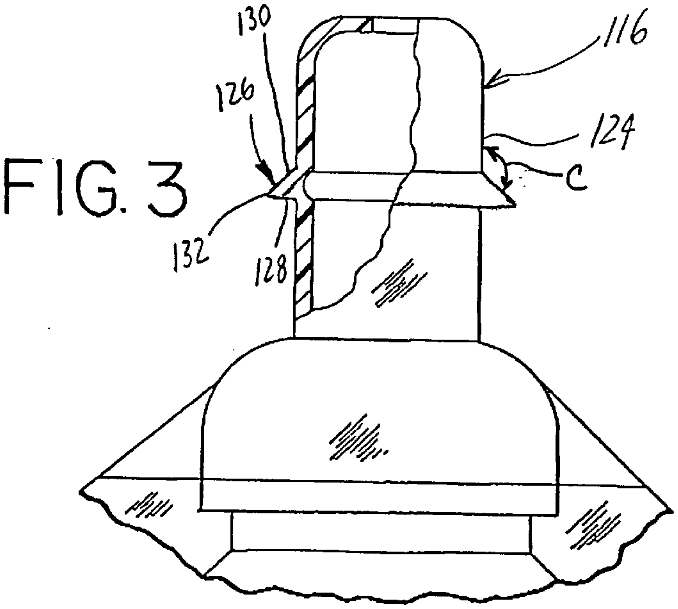
FIG. 3 is an enlarged fragmentary part sectional view of another nozzle embodiment in elevation.

The present invention is not limited to the particular triangular orientation of FIG. 2, of course, but rather encompasses all other suitable and desirable configurations such as, for example, a syncline configuration or the embodiment of FIG. 3 which shows a nozzle 116 including an outer nozzle surface 124 having a substantially triangularly shaped annular bead 126 extending circumferentially and radially outwardly therefrom. The bead 126 includes a lower flat surface 128 which extends unitarily generally normally outwardly from the outer surface 124 and a spaced-apart upper flat surface 130 which extends unitarily radially outwardly from the outer nozzle surface 124 at an obtuse angle C of approximately 160 degrees. The distal ends of the two surfaces 128 and 130 terminate in an annular edge 132.

Figure 4:
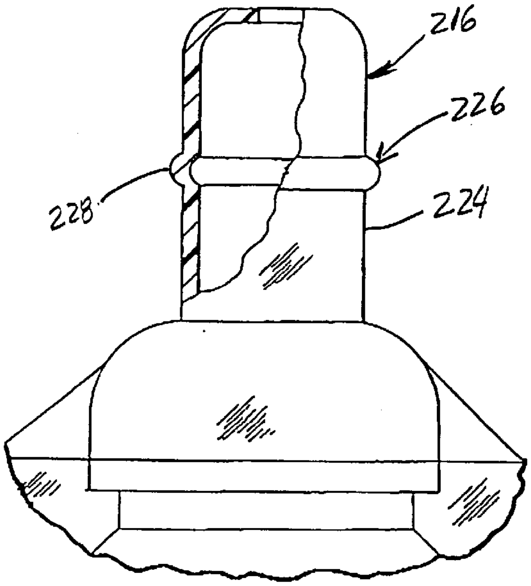
FIG. 4 is an enlarged fragmentary part sectional view of another nozzle embodiment in elevation.

FIG. 4 shows yet another nozzle embodiment 216 which includes an outer nozzle surface 224 having an annular bead 226 with a rounded surface 228.

Figure 5:
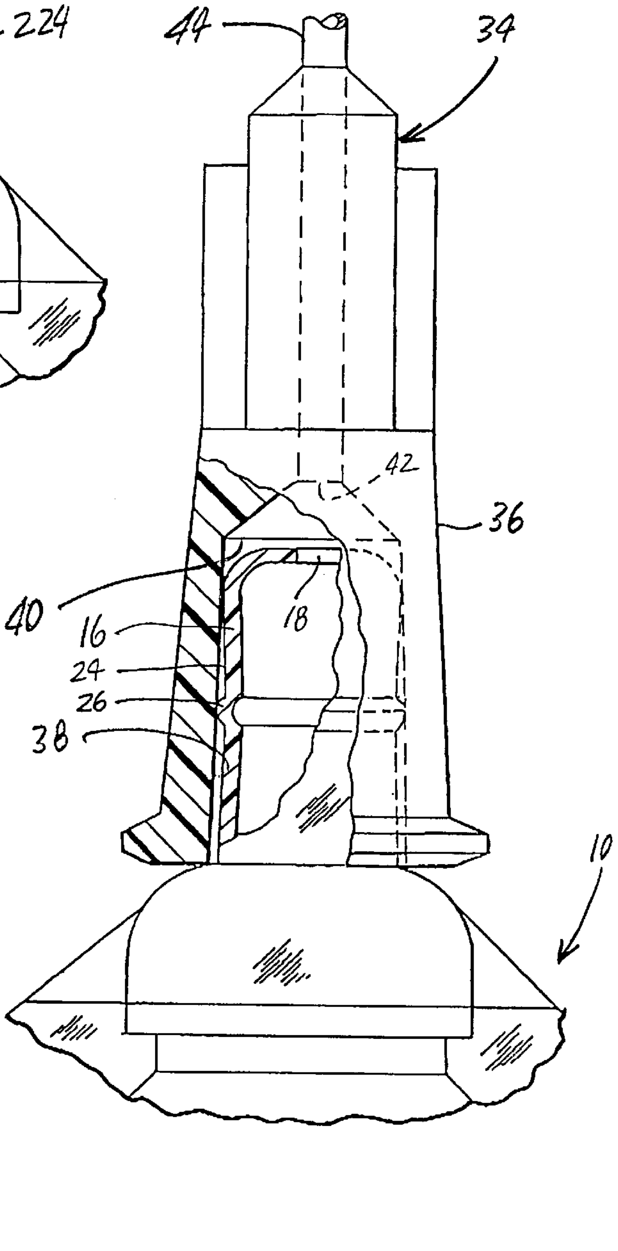
FIG. 5 is an enlarged fragmentary part sectional view of the container of FIG. 1 in elevation with the cap removed therefrom and a dispensing needle fitted over the nozzle.

As shown in FIG. 5, the container 10 of the present invention is adapted to be used together with a dispensing assembly 34, such as hypodermic needle assembly, including a female hub 36 with a luer tapered inner surface 38 which defines an interior hub cavity 40 and terminates in a dispensing or draining aperture 42. A dispensing needle 44 is mounted to the hub 36 and extends outwardly from the apertured end of the hub 36. According to the invention, the hub cavity 40 and the nozzle 16 are sized to allow the hub 36 to be fitted over the nozzle 16 as described below. The resilient bead 26 is sized such that its diameter, combined with the diameter of the nozzle 16, is slightly greater than the diameter of the hub cavity 40 in the region of engagement.

The container/dispensing assembly combination of FIG. 5 is particularly useful in medical applications which require the transfer or mixing of the contents of the container 10 with the contents of another container such as, for example, an intravenous bag. The needle assembly 34 provides for the quick and efficient transfer of liquid contents in such applications.

The transfer procedure, of course, initially includes the step of opening the container 10 by twisting off the overcap 20 about the frangible web 22 so as to expose draining aperture 18.

The needle assembly 34 is then securely fitted to the container 10. Particularly, the hub 36 thereof is received and fitted over the nozzle 16 in a mating relationship where a portion of the inner surface 38 of the hub 36 is in abutting and contiguous relationship with the outer surface 24 of the nozzle 16 and a portion of the inner surface 38 of the hub 36 is in abutting and contiguous relationship with the compressed annular edge 32 and surfaces 28 and 30 of the bead 26.

The resiliency and compressibility of the bead 26 and, more particularly, the resiliency and compressibility of the molded thermoplastic material comprising the same, allows the hub 36 to be pressed over the bead 26 which, in turn, comprises the bead 26 and allows the bead 26 to exert a sealing force against the inner surface 38 of the hub 36 to provide both a secure friction fit and liquid seal between the hub 36 and the nozzle 16.

Figure 6:
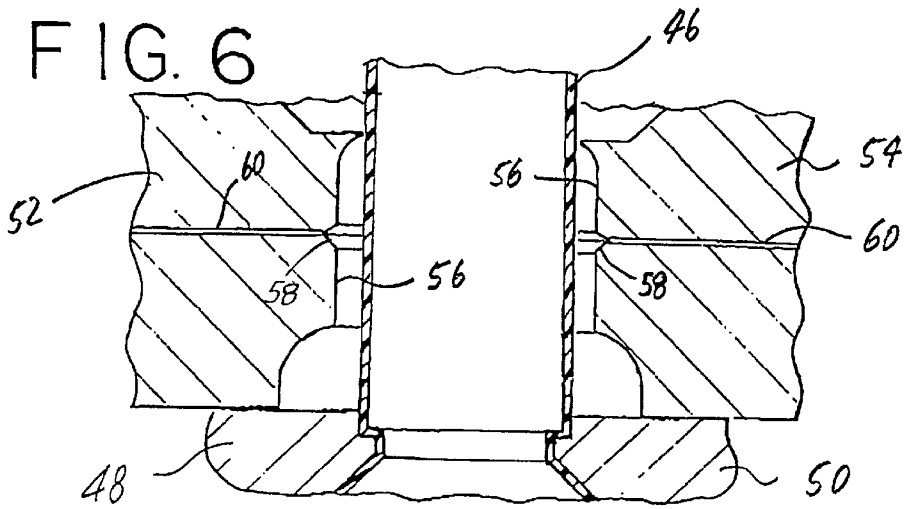
FIG. 6 is a fragmentary elevational view, partly in section, of the molds for forming the container of FIG. 1, the main molds being shown in their closed position for forming the container body portion and the seal molds in their open position.
Figure 7:
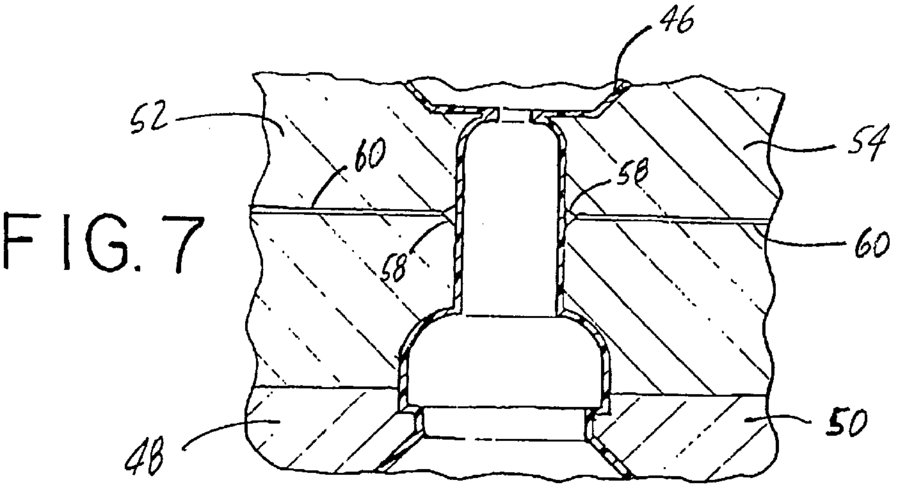
FIG. 7 is a fragmentary elevational view, partly in section, similar to that of FIG. 6 but showing the seal molds closed for forming the neck, nozzle and cap portions of the container.
Figure 8:
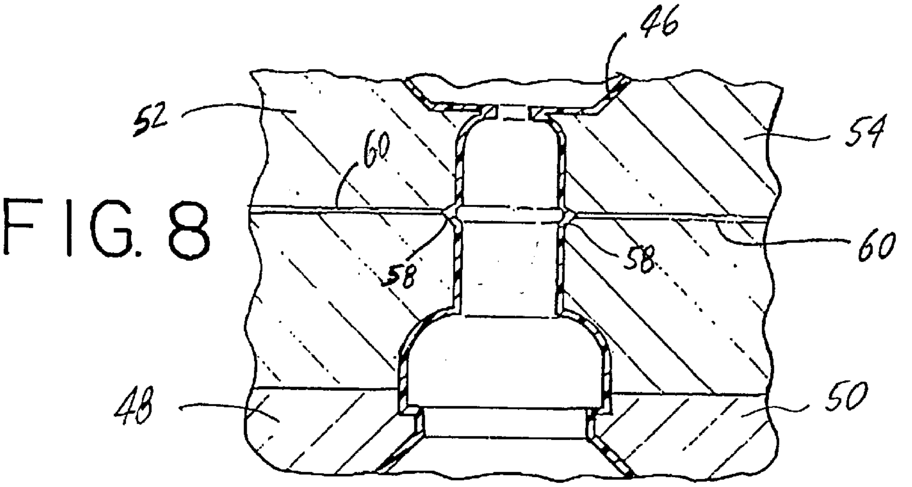
FIG. 8 is a fragmentary elevational view, partly in section, similar to FIG. 7 but additionally showing the parison in the groove in the seal molds for forming the bead on the nozzle.

The apparatus and method for fabricating a container with a beaded nozzle according to the present invention is shown in FIGS. 6–8. As shown in FIG. 7, a parison segment 46 is extruded as generally described in U.S. Pat. Nos. 4,671,763 and 4,707,966 to Weiler between main molds 48 and 50 and seal molds 52 and 54.

The main molds include complementary inner surfaces conforming to the exterior shape of the body portion 12 of the container 10 and the seal molds include complementary inner surfaces 56 conforming to the exterior shape of the neck portion 14, the nozzle 16, and the overcap 20 of the container 10. Additionally, each of the seal molds 52 and 54 include a groove 58 conforming to the exterior shape of the bead 26 on the nozzle 16 and a passage 60 extending from the groove 58 and through the body of the respective seal molds. Although not shown, it is understood that the mold apparatus further includes an operatively associated assembly for creating a vacuum in the passages 60.

The body portion 12 of the container 10 is formed and filled as shown in FIG. 6 in a known manner, for example, as also described in U.S. Pat. Nos. 4,671,763 and 4,707,966 to Weiler, the disclosures of which are incorporated herein by reference to the extent relevant and not inconsistent herewith.

Next, the seal molds 52 and 54 are closed as shown in FIG. 7 to form and seal the nozzle 16 and the overcap 20 in a known manner, for example, as also described in U.S. Pat. Nos. 4,671,763 and 4,707,966 to Weiler.

As shown in FIG. 8, however, the size and the width of the groove 58 in the seal molds 52 and 54 coupled with the thickness of the parison 46 is such that the closing of the seal molds 52 and 54 is not sufficient to cause the parison 46 to fill the groove 58 to form the bead 26. As a result, it is necessary to create a vacuum in the passages 60 and the groove 58 to pull a portion of the parison 46 into the groove 58 as shown in FIG. 8 to form the bead 26 as the container 10 is sealed.

The formed, filled and sealed container 10 is subsequently removed from the apparatus as also described in U.S. Pat. Nos. 4,671,763 and 4,707,966 to Weiler.

The foregoing specification and the drawings are to be taken as illustrative but not limiting of the present invention. Still other nozzle and bead configurations and other apparatus and methods utilizing the spirit and scope of the present invention are possible, and will readily present themselves to those skilled in the art.

I claim:

1. A hermetically sealed, molded thermoplastic dispensing container which comprises:

a nozzle unitary with the container and defining a dispensing aperture;

a removable closure unitary with the nozzle and occluding the aperture; and a resilient and compressible annular bead about the periphery of the nozzle, unitary therewith and spaced from the aperture;

said nozzle being adapted to receive the hub of a dispensing assembly in a mating relationship: the hub including an inner surface defining a cavity and said annular bead being sized such that the diameter thereof is greater than the diameter of the cavity defined in said hub whereby said bead is compressed when the hub is received over said bead and said bead exerts a sealing force against the inner surface of the hub in the region of engagement between the hub and the bead to provide a liquid seal between the hub and the nozzle in the region of engagement.

2. The container in accordance with claim 1 wherein the nozzle is sized to receive the hub of a dispensing assembly which is a hypodermic needle assembly.

3. The container in accordance with claim 1 wherein the nozzle is sized to receive the hub of a dispensing assembly wherein the hub surface in contact with the bead has a luer taper.

4. The container in accordance with claim 1 wherein said bead includes a rounded outer surface.

5. The container in accordance with claim 1 wherein said bead has a substantially triangular cross-section and includes spaced-apart upper and lower surfaces extending radially outwardly from said outer surface of said nozzle and respective distal ends which merge together to define an edge.

6. The container in accordance with claim 5 wherein each of said upper and lower surfaces extend radially outwardly from said outer surface of said nozzle at an obtuse angle.

7. The container in accordance with claim 6 wherein said lower surface of said bead extends radially outwardly from said outer surface of said nozzle at an obtuse angle greater than said upper surface of said bead.

8. The container in accordance with claim 6 wherein the obtuse angle between said outer surface of said nozzle and said upper surface of said bead is approximately 120 degrees while the obtuse angle between said outer surface of said nozzle and said lower surface of said bead is approximately 135 degrees.

9. The container in accordance with claim 5 wherein said lower surface of said bead extends radially outwardly from said outer surface of said nozzle substantially normal to the nozzle surface and said upper surface of said bead extends radially outwardly from said outer surface of said nozzle at an obtuse angle.

* * * * *